US010000625B2

(12) United States Patent
Ueki et al.

(10) Patent No.: US 10,000,625 B2
(45) Date of Patent: Jun. 19, 2018

(54) FLAME RETARDING AGENT, FLAME-RETARDANT AQUEOUS RESIN COMPOSITION AND FLAME-RETARDANT URETHANE RESIN COMPOSITION CONTAINING SAID FLAME-RETARDING AGENT, AND USE THEREFOR

(71) Applicant: Daihachi Chemical Industry Co., Ltd., Osaka-shi, Osaka (JP)

(72) Inventors: Takehiro Ueki, Higashiosaka (JP); Tomoe Takemoto, Higashiosaka (JP); Hiroshi Tsuji, Higashiosaka (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 728 days.

(21) Appl. No.: 14/411,906

(22) PCT Filed: Jun. 24, 2013

(86) PCT No.: PCT/JP2013/067266
§ 371 (c)(1),
(2) Date: Dec. 29, 2014

(87) PCT Pub. No.: WO2014/002958
PCT Pub. Date: Jan. 3, 2014

(65) Prior Publication Data
US 2015/0197624 A1    Jul. 16, 2015

(30) Foreign Application Priority Data

Jun. 28, 2012 (JP) ................. 2012-145979

(51) Int. Cl.
| | |
|---|---|
| C08K 5/00 | (2006.01) |
| C08K 5/5399 | (2006.01) |
| C09D 5/02 | (2006.01) |
| C09D 5/18 | (2006.01) |
| C09K 21/12 | (2006.01) |
| C09D 201/00 | (2006.01) |
| D06M 13/288 | (2006.01) |
| D06M 13/447 | (2006.01) |
| D06N 3/14 | (2006.01) |
| C08L 101/12 | (2006.01) |
| C07F 9/6571 | (2006.01) |

(Continued)

(52) U.S. Cl.
CPC ...... *C08K 5/5399* (2013.01); *C07F 9/657154* (2013.01); *C08L 101/12* (2013.01);
(Continued)

(58) Field of Classification Search
CPC .......... C08K 5/5399; C09D 5/02; C09D 5/18; C09D 175/04; C09D 7/1233;
(Continued)

(56) References Cited

U.S. PATENT DOCUMENTS

| 4,007,236 A | 2/1977 | Duffy et al. |
| 2004/0266916 A1 | 12/2004 | Harashina et al. |

(Continued)

FOREIGN PATENT DOCUMENTS

| CN | 1849422 A | 10/2006 |
| CN | 101608348 A | 12/2009 |

(Continued)

OTHER PUBLICATIONS

Taiwanese Office Action dated Mar. 9, 2017 in Taiwan Patent Application No. 102123266 (counterpart to U.S. Appl. No. 14/411,906) (7 pages) (Chinese only).
S. Wagner et al., "Synthesis of New Organophosphorus Compounds Using the Atherton-Todd Reaction as a Versatile Tool," Heteroatom Chemistry, vol. 23, No. 2, 2012 (7 pages).
PCT International Search Report from PCT/JP2013/067266, dated Sep. 2013 (5 pages).
European Office Action dated Apr. 6, 2017 in counterpart application No. 13809898.3 (4 pages).

*Primary Examiner* — Cephia D Toomer
(74) *Attorney, Agent, or Firm* — Flaster/Greenberg P.C.

(57) ABSTRACT

The present invention relates to a flame-retarding agent comprising a phosphoramidate compound represented by Formula (I):

[Chem. 1]

$$\begin{array}{c}R_1\\ \phantom{x}\\ R_2\end{array}\!\!>\!\!C\!\!<\!\!\begin{array}{c}R_{11}\!-\!O\\ \phantom{x}\\ R_{12}\!-\!O\end{array}\!\!>\!\!\overset{\displaystyle O}{\underset{\displaystyle P}{\|}}\!\!<\!\!\begin{array}{c}R_{13}\!-\!A\\ \phantom{x}\\ B_1\end{array} \quad (I)$$

wherein $R_1$ and $R_2$ are each independently $C_{1-3}$ alkyl, $R_{11}$ and $R_{12}$ are each independently $C_{1-3}$ alkylene, $R_{13}$ is $C_{1-6}$ alkylene, $B_1$ is hydrogen or $C_{1-6}$ alkyl, and A is hydrogen or an organic group represented by Formula (Ia):

[Chem. 2]

$$\begin{array}{c}B_2\\ \phantom{x}\\ \end{array}\!\!>\!\!N\!\!-\!\!\overset{\displaystyle O}{\underset{\displaystyle P}{\|}}\!\!<\!\!\begin{array}{c}O\!-\!R_{14}\\ \phantom{x}\\ O\!-\!R_{15}\end{array}\!\!>\!\!C\!\!<\!\!\begin{array}{c}R_3\\ \phantom{x}\\ R_4\end{array} \quad (Ia)$$

wherein $R_3$ and $R_4$ are each independently $C_{1-3}$ alkyl, $R_{14}$ and $R_{15}$ are each independently $C_{1-3}$ alkylene, and $B_2$ is hydrogen or $C_{1-6}$ alkyl,
wherein when $B_1$ is $C_{1-6}$ alkyl, and A is hydrogen, $B_1$ and $R_{13}$-A, taken together with nitrogen to which they are attached, may form a non-aromatic nitrogen-containing heterocycle, and
wherein when $B_1$ is $C_{1-6}$ alkyl, A is an organic group represented by Formula (Ia), and $B_2$ is $C_{1-6}$ alkyl, $B_1$ and $B_2$, taken together with nitrogen to which they are attached and with $R_{13}$, may form a non-aromatic nitrogen-containing heterocycle.

11 Claims, No Drawings

(51) Int. Cl.
*C09D 175/04* (2006.01)
*C09J 175/04* (2006.01)
*D06N 3/00* (2006.01)
*C09D 133/08* (2006.01)
*D06M 13/44* (2006.01)

(52) U.S. Cl.
CPC ............... *C09D 5/02* (2013.01); *C09D 5/18* (2013.01); *C09D 7/63* (2018.01); *C09D 133/08* (2013.01); *C09D 175/04* (2013.01); *C09D 201/00* (2013.01); *C09J 175/04* (2013.01); *C09K 21/12* (2013.01); *D06M 13/288* (2013.01); *D06M 13/447* (2013.01); *D06N 3/0059* (2013.01); *D06N 3/14* (2013.01); *C08G 2190/00* (2013.01); *D06M 13/44* (2013.01); *D06N 2209/067* (2013.01); *D06N 2211/28* (2013.01); *Y10T 428/249921* (2015.04); *Y10T 442/268* (2015.04)

(58) Field of Classification Search
CPC .............. C09D 133/08; D06M 13/288; D06M 13/447; D06M 13/44; D06N 3/14; D06N 3/0059; D06N 2211/28; C09K 21/12; C08L 101/12; C07F 9/657154; C09J 175/04; C08G 2190/00; Y10T 428/249921; Y10T 442/268
See application file for complete search history.

(56) References Cited

U.S. PATENT DOCUMENTS

| | | |
|---|---|---|
| 2007/0009723 A1 | 1/2007 | Ogawa et al. |
| 2007/0259582 A1 | 11/2007 | Ohara |
| 2010/0063169 A1 | 3/2010 | Stowell et al. |

FOREIGN PATENT DOCUMENTS

| | | |
|---|---|---|
| CN | 101381445 B | 8/2011 |
| EP | 1916329 A1 | 4/2008 |
| JP | 47-002581 U | 8/1972 |
| JP | 51-091277 A | 8/1976 |
| JP | 54019919 * | 2/1979 |
| JP | 06-146174 A | 5/1994 |
| JP | 2004-169197 A | 6/2004 |
| JP | 2005-162912 A | 6/2005 |
| JP | 2006-063125 A | 3/2006 |
| JP | 2006-233152 A | 9/2006 |
| JP | 2011-236284 A | 11/2011 |
| JP | 2012-229508 A | 11/2012 |
| WO | WO 03/046083 A1 | 5/2003 |
| WO | WO 03/048247 A1 | 6/2003 |
| WO | WO 2008/085926 A1 | 7/2008 |

* cited by examiner

# FLAME RETARDING AGENT, FLAME-RETARDANT AQUEOUS RESIN COMPOSITION AND FLAME-RETARDANT URETHANE RESIN COMPOSITION CONTAINING SAID FLAME-RETARDING AGENT, AND USE THEREFOR

BACKGROUND OF THE INVENTION

Field of the Invention

The present invention relates to a flame-retarding agent, a flame-retardant aqueous resin composition containing the flame-retarding agent, a flame-retardant urethane resin composition containing the flame-retarding agent, and the use therefor. More specifically, the present invention relates to a flame-retarding agent containing a phosphoramidate compound having a specific structure, and a flame-retardant aqueous resin composition that contains this flame-retarding agent and that can be suitably used for a flame-retardant back-coating agent, a flame-retardant coating agent, and other agents. The present invention also relates to a coating agent using this flame-retardant aqueous resin composition and a back-coating agent using this flame-retardant aqueous resin composition, and flame-retardant fiber fabric back-coated with this back-coating agent, as well as a flame-retardant urethane resin composition containing this flame-retarding agent, and a synthetic leather using this flame-retardant urethane resin composition.

Description of Related Art

Hitherto, the back surface of fiber interior materials for vehicles (automobiles, railway vehicles), airplanes, and the like, is subjected to back-coating (backing treatment; backing process), i.e., a back-coating agent (backing agent) is applied to the back surface, to inhibit shedding of the fiber and to increase the strength. To address safety issues, the use of materials to which flame-retardancy is imparted is currently demanded in fields of, in particular, automobiles, etc., and back-coating agents used for these materials are also required to achieve high flame retardancy. Examples of general-purpose flame-retarding agents used in back-coating agents include a halogen-based flame-retarding agent, such as decabromodiphenyl ether combined with antimony oxide.

Although a halogen-based flame-retarding agent generally has excellent properties as a flame-retarding agent, because they contain halogen elements, such as chlorine and bromine, when a product obtained by using a back-coating agent containing such a halogen-based flame-retarding agent is discarded and burnt, hydrogen halide, which is an environmentally hazardous substance, is problematically generated. Further, depending on the type of the halogen-based flame-retarding agent, a substance with greater environmental load, such as halogenated dioxin, is problematically generated. For this reason, avoiding the use thereof or using a reduced amount thereof is desired.

Other than the halogen-based flame-retarding agents, polyphosphate-based flame-retarding agents are effective as a flame-retarding agent. However, polyphosphate-based flame-retarding agents have insufficient water resistance; in particular, they cause problems such as water spots (kiwatsuki) on the surface of fiber products, deteriorating the texture of the products. The term "water spots" as used herein refers to a phenomenon in which high-temperature vapor used in the production of seats for vehicles, as well as moisture, such as rain and sweat, adhere to the surface of a fiber product and allow dissolution of the water-soluble components of the flame-retarding agent, causing the wetted portion to turn into white spots or a stain after drying. To inhibit the formation of water spots, various attempts have been made, such as coating the surface of a polyphosphate-based flame-retarding agent with a silicone compound or a melamine resin (Patent Literature (PTL) 1 and Patent Literature 2). These methods remarkably lessen the formation of water spots caused by ordinary-temperature water; however, the formation of water spots caused by high-temperature vapor or high-temperature water is not sufficiently prevented. To prevent water spots from forming, a compound having low solubility in hot water is in demand, since solubility in hot water is the cause of water spot formation.

In addition to polyphosphate-based flame-retarding agents, there are other flame-retarding agents that contain phosphorus. Among them, phosphoric acid ester-based flame-retarding agents are widely used for, for example, molding resin, urethane foam, and fiber. Some compounds among the phosphoric acid ester-based flame-retarding agents have excellent water resistance. However, many compounds among the phosphoric acid ester-based flame-retarding agents have insufficient flame retardancy when used for back-coating.

Further, synthetic leather has recently been used as a fiber interior material of automobiles, etc., and is also required to have high flame retardancy. As a flame-retarding agent used for synthetic leather, a halogen-based flame-retarding agent, similar to the above back-coating agent, was used; there was, however, an environmental issue since a halogenated gas is generated when the halogen-based flame-retarding agent is burnt, as stated above.

In view of the above, phosphoric acid ester-based flame-retarding agents have been studied (PTL 3 and PTL 4) as effective flame-retarding agents other than halogen-based flame-retarding agents. However, phosphoric acid ester-based flame-retarding agents generally have an unsatisfactory flame-retardant effect, compared with halogen-based flame-retarding agents. To achieve high flame retardancy by using only a phosphoric acid ester-based flame-retarding agent, the use of a special flame-retarding agent and an increase in the amount of the flame-retarding agent are necessary. In either case, the increase in the production cost was problematic.

CITATION LIST

Patent Literature

PTL 1: JP2006-063125A
PTL 2: JP2006-233152A
PTL 3: JPH06-146174A
PTL 4: JP2011-236284A

BRIEF SUMMARY OF THE INVENTION

Technical Problem

An object of the present invention is to provide a flame-retarding agent that is halogen-free, that has excellent flame retardancy, and that does not cause the formation of water spots, and an aqueous resin composition containing the flame-retarding agent. Another object of the present invention is to provide a coating agent and a back-coating agent using the flame-retardant aqueous resin composition, and a flame-retardant fiber fabric back-coated with this back-coating agent. Still another object of the present invention is to provide a flame-retardant urethane resin composition containing the flame-retarding agent, and a flame-retardant synthetic leather using this flame-retardant urethane resin composition.

Solution to Problem

In order to achieve the above objects, the present inventors conducted extensive research, and found that a phosphoramidate compound having a specific structure, i.e., a halogen-free structure, has excellent flame retardancy and low solubility in hot water, which is the cause of water spot formation, and that therefore, the use of this phosphoramidate compound as a flame-retarding agent can achieve the above objects. The present invention is thereby accomplished.

More specifically, the present invention provides the following flame-retarding agent, flame-retardant aqueous resin composition, flame-retardant urethane resin composition, and the like.

Item 1. A flame-retarding agent comprising a phosphoramidate compound represented by Formula (I):

[Chem. 1]

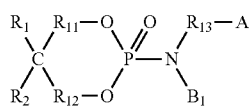

wherein $R_1$ and $R_2$ are each independently $C_{1-3}$ alkyl, $R_{11}$ and $R_{12}$ are each independently $C_{1-3}$ alkylene, $R_{13}$ is $C_{1-6}$ alkylene, $B_1$ is hydrogen or $C_{1-6}$ alkyl, and A is hydrogen or an organic group represented by Formula (Ia):

[Chem. 2]

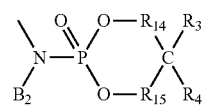

wherein $R_3$ and $R_4$ are each independently $C_{1-3}$ alkyl, $R_{14}$ and $R_{15}$ are each independently $C_{1-3}$ alkylene, and $B_2$ is hydrogen or $C_{1-6}$ alkyl, wherein when $B_1$ is $C_{1-6}$ alkyl, and A is hydrogen, $B_1$ and $R_{13}$-A, taken together with nitrogen to which they are attached, may form a non-aromatic nitrogen-containing heterocycle, and wherein when $B_1$ is $C_{1-6}$ alkyl, A is an organic group represented by Formula (Ia), and $B_2$ is $C_{1-6}$ alkyl, $B_1$ and $B_2$, taken together with nitrogen to which they are attached and with $R_{13}$, may form a non-aromatic nitrogen-containing heterocycle.

Item 2. The flame-retarding agent according to Item 1, wherein in Formula (I), $R_1$ and $R_2$ represent methyl, and $R_{11}$ and $R_{12}$ represent methylene.

Item 3. The flame-retarding agent according to Item 1 or 2, wherein A of Formula (I) is an organic group represented by Formula (Ia), wherein $R_3$ and $R_4$ represent methyl, and $R_{14}$ and $R_{15}$ represent methylene.

Item 4. The flame-retarding agent according to Item 3, wherein $R_{13}$ of Formula (I) is $C_{1-4}$ alkylene.

Item 5. The flame-retarding agent according to Item 4, wherein $R_{13}$ of Formula (I) is $C_{1-2}$ alkylene.

Item 6. The flame-retarding agent according to any one of Items 3 to 5, wherein in Formula (I), $B_1$ and $B_2$ represent hydrogen.

Item 7. The flame-retarding agent according to any one of Items 3 to 5, wherein in Formula (I), $B_1$ and $B_2$, taken together with nitrogen to which they are attached and with $R_{13}$, form a 5- to 8-membered non-aromatic nitrogen-containing heterocycle.

Item 8. A flame-retardant aqueous resin composition comprising the flame-retarding agent of any one of Items 1 to 7 and an aqueous resin emulsion.

Item 9. A back-coating agent comprising the flame-retardant aqueous resin composition of Item 8.

Item 10. A flame-retardant fiber fabric back-coated with the back-coating agent of Item 9.

Item 11. A coating agent comprising the flame-retardant aqueous resin composition of Item 8.

Item 12. A flame-retardant urethane resin composition for synthetic leather, the composition comprising the flame-retarding agent of any one of Items 1 to 7, a polyol, and an isocyanate.

Item 13. A flame-retardant synthetic leather having on at least one surface of a base fabric a layer containing the flame-retardant urethane resin composition of Item 12.

Item 14. The flame-retardant synthetic leather according to Item 13, wherein the flame-retardant synthetic leather comprises at least a base fabric, an adhesive layer, and a surface skin layer in this order, and the adhesive layer is formed of the flame-retardant urethane resin composition of Item 12.

Advantageous Effects of Invention

The flame-retarding agent of the present invention comprises a halogen-free phosphoramidate compound, and is thus environmentally friendly. This phosphoramidate compound shows excellent flame retardancy and has low solubility in hot water, which is the cause of water spot formation. Therefore, the use of the flame-retarding agent comprising this phosphoramidate compound enables provision of a flame-retardant aqueous resin composition, a back-coating agent, and a coating agent, that have excellent flame retardancy and that form no water spots, as well as a flame-retardant urethane resin composition and a flame-retardant synthetic leather, that have excellent flame retardancy.

DETAILED DESCRIPTION OF THE INVENTION

The flame-retarding agent of the present invention comprises a phosphoramidate compound represented by Formula (I):

[Chem. 3]

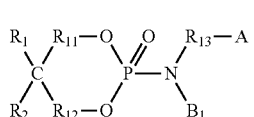

wherein $R_1$ and $R_2$ are each independently $C_{1-3}$ alkyl, $R_{11}$ and $R_{12}$ are each independently $C_{1-3}$ alkylene, $R_{13}$ is $C_{1-6}$ alkylene, $B_1$ is hydrogen or $C_{1-6}$ alkyl, and A is hydrogen or an organic group represented by Formula (Ia):

[Chem. 4]

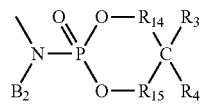

(Ia)

wherein $R_3$ and $R_4$ are each independently $C_{1-3}$ alkyl, $R_{14}$ and $R_{15}$ are each independently $C_{1-3}$ alkylene, and $B_2$ is hydrogen or $C_{1-6}$ alkyl, wherein when $B_1$ is $C_{1-6}$ alkyl, and A is hydrogen, $B_1$ and $R_{13}$-A, taken together with nitrogen to which they are attached, may form a non-aromatic nitrogen-containing heterocycle, and wherein when $B_1$ is $C_{1-6}$ alkyl, A is an organic group represented by Formula (Ia), and $B_2$ is $C_{1-6}$ alkyl, $B_1$ and $B_2$, taken together with nitrogen to which they are attached and with $R_{13}$, may form a non-aromatic nitrogen-containing heterocycle.

Examples of the $C_{1-3}$ alkyl in Formula (I) include methyl, ethyl, n-propyl, and isopropyl. Of these, methyl and ethyl are preferable, with methyl being particularly preferable from the viewpoint of flame retardancy. Examples of the $C_{1-3}$ alkylene include methylene, ethylene, n-propylene, and isopropylene. Of these, methylene and ethylene are preferable, with methylene being particularly preferable from the viewpoint of flame retardancy.

Examples of the $C_{1-6}$ alkyl include methyl, ethyl, n-propyl, isopropyl, n-butyl, isobutyl, tert-butyl, n-pentyl, n-hexyl, and the like. Of these, methyl and ethyl are preferable, with methyl being particularly preferable from the viewpoint of flame retardancy. Examples of the $C_{1-6}$ alkylene include methylene, ethylene, n-propylene, isopropylene, n-butylene, isobutylene, tert-butylene, n-pentylene, n-hexylene, and the like. Of these, alkylene having 4 carbon atoms or less is preferable, with methylene and ethylene being particularly preferable from the viewpoint of flame retardancy.

The non-aromatic nitrogen-containing heterocycle formed when A is hydrogen is a 3- to 13-membered, preferably 4- to 8-membered, heterocycle containing one nitrogen atom.

The non-aromatic nitrogen-containing heterocycle formed when A is an organic group represented by Formula (Ia) is a 5- to 20-membered, preferably 5- to 8-membered, heterocycle containing two nitrogen atoms.

Examples of the phosphoramidate compound represented by Formula (I) include the following:

those wherein A is hydrogen, i.e., compounds represented by Formula (II):

[Chem. 5]

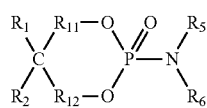

(II)

wherein $R_1$, $R_2$, $R_{11}$, and $R_{12}$ are as defined above for Formula (I), $R_5$ is $C_{1-6}$ alkyl, and $R_6$ is $C_{1-6}$ alkyl or hydrogen;

those wherein $B_1$ is $C_{1-6}$ alkyl, A is hydrogen, and $B_1$ and $R_{13}$-A, taken together with nitrogen to which they are attached, form a non-aromatic nitrogen-containing heterocycle, i.e., compounds represented by Formula (III):

[Chem. 6]

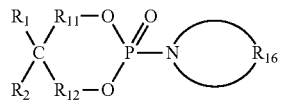

(III)

wherein $R_1$, $R_2$, $R_{11}$, and $R_{12}$ are as defined for Formula (I), and $R_{16}$ is $C_{2-12}$ alkylene;

those wherein A is an organic group represented by Formula (Ia), and $B_1$ and $B_2$ are each independently hydrogen or $C_{1-6}$ alkyl, i.e., compounds represented by Formula (IV):

[Chem. 7]

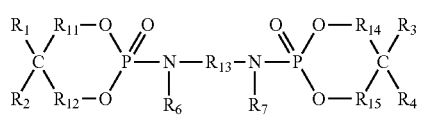

(VI)

wherein $R_1$, $R_2$, $R_{11}$, $R_{12}$, and $R_{13}$ are as defined for Formula (I), $R_3$, $R_4$, $R_{14}$, and $R_{15}$ are as defined for Formula (Ia), $R_6$ and $R_7$ are each independently hydrogen or $C_{1-6}$ alkyl; those wherein $B_1$ is $C_{1-6}$ alkyl, A is an organic group represented by Formula (Ia), $B_2$ is $C_{1-6}$ alkyl, and $B_1$ and $B_2$, taken together with nitrogen to which they are attached and with $R_{13}$, form a non-aromatic nitrogen-containing heterocycle, i.e., compounds represented by Formula (V):

[Chem. 8]

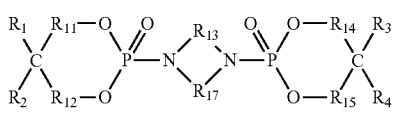

(V)

wherein $R_1$, $R_2$, $R_{11}$, $R_{12}$, and $R_{13}$ are as defined for Formula (I), $R_3$, $R_4$, $R_{14}$, $R_{15}$ are as defined for Formula (Ia), and $R_{17}$ is $C_{2-12}$ alkylene; and the like.

Examples of the compounds represented by Formula (II) include compounds represented by the following Formulae (1) to (5), and the like. Examples of the compounds represented by Formula (III) include compounds represented by the following Formulae (6) to (8), and the like. Examples of the compounds represented by Formula (IV) include compounds represented by the following Formulae (9) to (13), and the like. Examples of the compounds represented by Formula (V) include compounds represented by the following Formulae (14) to (18), and the like.

[Chem. 9]

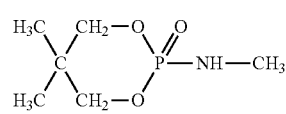

(1)

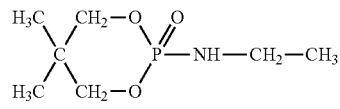

(2)

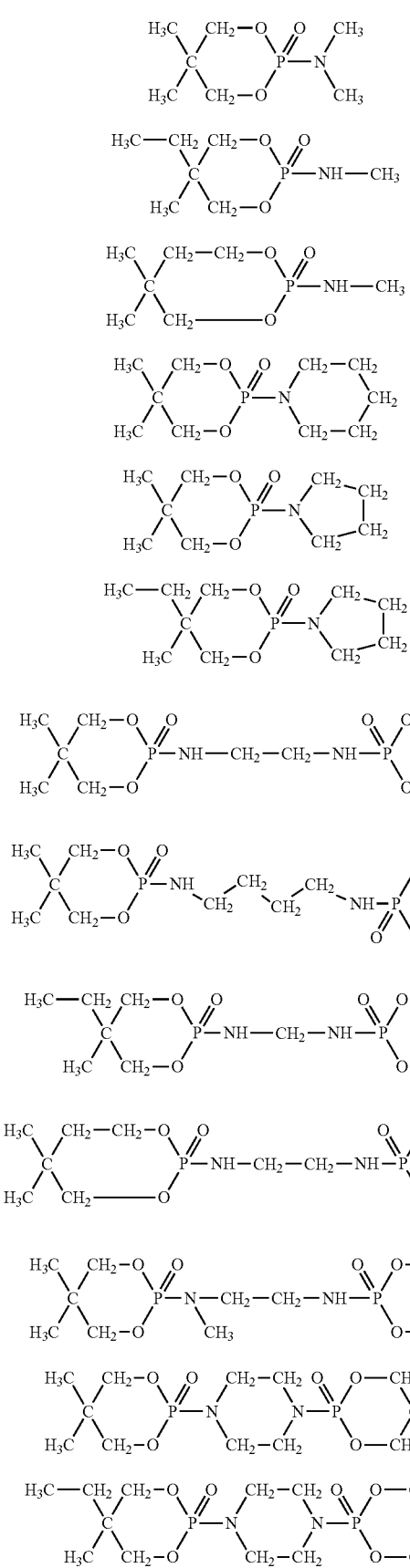

Among the phosphoramidate compounds represented by Formula (I), a compound of Formula (I), wherein $R_1$ and $R_2$ represent methyl, and $R_{11}$ and $R_{12}$ represent methylene, is preferable from the viewpoint of flame retardancy.

A of Formula (I) is preferably an organic group represented by Formula (Ia). From the viewpoint of flame retardancy, $R_3$ and $R_4$ preferably represent methyl, and $R_{14}$ and $R_{15}$ preferably represent methylene.

$R_{13}$ of Formula (I) preferably has 1 to 4 carbon atoms, and still more preferably 1 to 2 carbon atoms, from the viewpoint of flame retardancy.

From the viewpoint of flame retardancy, when A of Formula (I) is an organic group represented by Formula (Ia), it is preferable that $B_1$ of Formula (I) and $B_2$ of Founula (Ia) represent hydrogen when $B_1$ and $B_2$ are not attached to each other; when $B_1$ and $B_2$ are attached to each other, it is preferable that $B_1$ and $B_2$ form ethylene, and taken together with nitrogen to which they are attached and with $R_{13}$, form a 5- to 8-membered non-aromatic nitrogen-containing heterocycle.

Among compounds represented by Formulae (1) to (18) above, the compounds represented by Formulae (9) to (11), (14), and (16) are preferable, with compounds represented by Formulae (9) and (14) being more preferable.

These phosphoramidate compounds have excellent flame retardancy and low solubility in hot water. Flame-retardant fabric back-coated with a flame-retardant aqueous resin composition comprising one or more of these phosphoramidate compounds shows excellent flame retardancy, and is free from water spots.

These phosphoramidate compounds may be used singly, or in a combination of two or more types thereof The phosphoramidate compound, which is the flame-retarding agent of the present invention, preferably has a small particle diameter to achieve uniform application of a back-coating agent or coating agent comprising the flame-retardant aqueous resin composition. Specifically, the phosphoramidate compound has an average particle diameter of 50 µm or less, and more preferably 20 µm or less.

If the phosphoramidate compound represented by Formula (I) is incorporated in an overly small amount, the flame retardancy will be insufficient. If the phosphoramidate compound represented by Formula (I) is incorporated in an overly large amount, the strength or the texture of a back coat layer will deteriorate. Therefore, the phosphoramidate compound is incorporated in an amount of preferably 5 to 80 wt %, more preferably 20 to 70 wt %, and particularly preferably 40 to 60 wt %, of the total solids content of the flame-retardant aqueous resin composition.

Examples of the method for synthesizing the phosphoramidate compound represented by Formula (I) include, but are not particularly limited to, a method comprising reacting a compound represented by Formula (VI):

[Chem. 10]

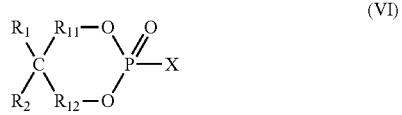

(VI)

wherein $R_1$, $R_2$, $R_{11}$, and $R_{12}$ are as defined above for Formula (I), and X is halogen, such as Br and Cl, with a corresponding amine compound.

Specifically, when the phosphoramidate compound is represented by Formula (II), it is sufficient if the compound of Formula (VI) is reacted with an amine (e.g., methylamine) at a ratio of 1:1 (molar ratio). When the phosphoramidate compound is represented by Formula (III), it is sufficient if the compound of Formula (VI) is reacted with a cyclic amine (e.g., piperidine) at a ratio of 1:1 (molar ratio). When the phosphoramidate compound is represented by Formula (IV), it is sufficient if the compound of Formula (VI) is reacted with a diamine (e.g., ethylenediamine) at a ratio of 2:1 (molar ratio). When the phosphoramidate compound is represented by Formula (V), it is sufficient if the compound of Formula (VI) is reacted with a cyclic diamine (e.g., piperazine) at a ratio of 2:1 (molar ratio).

The flame-retardant aqueous resin composition of the present invention may be prepared by mixing and stirring the above phosphoramidate compound and an aqueous resin emulsion, and optionally additives, such as a thickener.

The aqueous resin emulsion used in the present invention is a dispersion of fine particles of a synthetic resin in water. The aqueous resin emulsion can be produced by subjecting a starting monomer to emulsion polymerization in an aqueous media. Commercially available products of an aqueous resin emulsion generally used for textile processing may also be suitably used. The aqueous media used in the production of the aqueous resin emulsion is water containing various additives. The additives may be known additives used in a production method comprising emulsion polymerization of various polymers. Examples of specific additives include catalyst, emulsifier, chain transfer agent, and the like. The reaction conditions of emulsion polymerization is not particularly limited, and may be appropriately set according to the type of monomers, the type of additives, and the like. It is preferable to use an aqueous resin emulsion containing an acrylic-based or urethane-based resin as the synthetic resin.

The flame-retardant aqueous resin composition of the present invention has a solids content of preferably 30 to 70 wt %, and more preferably 40 to 60 wt %.

The flame-retardant aqueous resin composition of the present invention may further comprise a thickener to improve the processing stability. Examples of the thickener include carboxymethyl cellulose (CMC), hydroxyethyl cellulose (HEC), starch, xanthan gum, gum arabic, sodium alginate, polyvinyl alcohol, gelatin, polyvinylpyrrolidone, acrylic-based copolymer resin, urethane-modified surfactant, and the like. When thickened, the flame-retardant aqueous resin composition preferably has a viscosity of 5,000 to 50,000 mPa·s.

The flame-retardant aqueous resin composition of the present invention may additionally comprise a flame-retarding agent other than the phosphoramidate compound having the structure of Formula (I), as long as the object of the present invention is not impaired. Examples of a flame-retarding agent other than the phosphoramidate compound having the structure of Formula (I) include ammonium polyphosphate, aluminum hydroxide, magnesium hydroxide, phosphoric acid ester, alkyl phosphiric acid metal salt, and the like.

The flame-retardant aqueous resin composition of the present invention may optionally comprise various additives. Examples of the additives include UV absorber, antioxidant, light stabilizer, pigment, surface modifier, antimicrobial agent, insect repellent, antistatic agent, and the like.

The operation of mixing and stirring may be performed by using a commonly used stirring device, such as a variety of mills and homogenizers. There is no limitation to the order of the addition as long as the components are uniformly mixed. It is possible to place all of the components into a stirring device at once to perform mixing and stirring. It is also possible to add a phosphoramidate compound to the aqueous resin emulsion while it is being stirred.

The flame-retardant aqueous resin composition of the present invention may be suitably used for compositions and materials, such as a back-coating agent and a coating agent, in various fields that are required to have flame retardancy. Therefore, in another embodiment of the present invention, a back-coating agent and a coating agent, each comprising the flame-retardant aqueous resin composition of the present invention, are provided. The back-coating agent and coating agent, each comprising the flame-retardant aqueous resin composition, contain the above phosphoramidate compound, and thus show excellent flame retardancy and have low solubility in hot water.

Examples of fiber fabrics to which the back-coating agent of the present invention is applied include woven fabric and knitted fabric made of natural fibers, such as cotton, hemp, silk, and wool; regenerated fibers, such as rayon and acetate; synthetic fibers, such as polyamide, polyvinyl chloride, polyacrylonitrile, and polyester; and the like.

The method for applying the back-coating agent of the present invention to the back of cloth (fabric) is not particularly limited, and a known application method, such as a method using a roll coater, knife coater, blade coater, bar coater, or calender coater, may be used.

The amount of the back-coating agent applied to fiber varies depending on the usage of flame-retardant fiber fabric, the required flame resistance level, and the like. For the usage of a vehicle seat surface skin, the dry solids content is preferably 20 to 200 g/m². If it is less than 20 g/m², sufficient flame retardancy cannot be imparted, and if it exceeds 200 g/m², the texture may be hardened.

Drying is preferably performed after application under conditions at a temperature of 100 to 180° C. for 1 to 10 minutes.

The thus-obtained fiber fabric back-coated with the back-coating agent comprising the flame-retardant aqueous resin composition shows excellent flame retardancy, and is free from water spots.

The phosphoramidate compound, which is the flame-retarding agent of the present invention, has excellent flame retardancy. When this flame-retarding agent is added to a urethane resin composition to obtain a flame-retardant urethane resin composition, and when the obtained flame-retardant urethane resin composition is used, it is possible to obtain a synthetic leather having flame retardancy.

The flame-retardant urethane resin composition of the present invention is a polyurethane resin composition comprising a polyol, an isocyanate, and a phosphoramidate compound, which is a flame-retarding agent. The urethane resin composition of the present invention comprises a phosphoramidate compound having excellent flame retardancy, and thus shows excellent flame retardancy. Therefore, the urethane resin composition of the present invention may be used as a constituent resin of a flame-retardant urethane film, a flame-retardant urethane-based adhesive agent, a flame-retardant urethane-based sealant, a flame-retardant urethane-based coating composition, and the like. However, the urethane resin composition of the present invention is not suitable for a foaming polyurethane foam, since the form and the required properties are different.

The urethane resin composition of the present invention may either be thermoplastic or thermosetting, as long as it contains the above phosphoramidate compound to show flame retardancy. The form of the urethane resin composition may be solvent-free (non-solvent based), hot melt-based, solvent-based, or water-based, and may also be a one-part or two-part curable type. The form is suitably selected according to the purpose and the usage.

There is no particular limitation to the polyol used to constitute the urethane resin composition of the present invention, as long as it is a hitherto known component for constituting urethane resin. Examples of the polyol used in the present invention include polyether polyol, polyester polyol, polycarbonate polyol, polycaprolactone polyol, and the like. These polyols may be present alone, or in a combination of two or more (including polycondensation products) in the urethane resin. As described above, the polyol used in the present invention may be suitably selected from polyols generally used in the production of urethane resin.

Examples of the polyether polyol include polyethylene glycol, polypropylene glycol, polytetramethylene glycol, poly-2-methyltetramethylene glycol, and the like.

Examples of the polyester polyol include condensation products of adipic acid and polyhydric alcohol, such as polybutanediol adipate, poly-3-methylpentanediol adipate, poly-1,6-hexanediol adipate, and polyneopentylglycol adipate; esterified products of alkylene diol, neopentyl glycol, 1,6-hexanediol, dimethylolheptyne, and nonanediol, with dibasic acids, such as sebacic acid, azelaic acid, isophthalic acid, and phthalic acid; and the like.

Examples of the polycarbonate polyol include poly-1,6-hexanediol carbonate, as well as polyalkylene carbonate polyol obtained by synthesizing appropriately combined alkylene glycols, such as propylene glycol, butanediol, pentanediol, hexanediol, 3-methyl pentanediol, cyclohexanedimethanol, octanediol, nonanediol, and decanediol.

Examples of polysiloxane polyol include dimethyl polysiloxane polyol, methylphenyl polysiloxane polyol, and the like.

There is no particular limitation to the isocyanate used to constitute the urethane resin composition of the present invention, as long as it is a hitherto known component for constituting urethane resin. Examples include tolylene diisocyanate (hereinafter sometimes referred to as "TDI"), isophorone diisocyanate (hereinafter sometimes referred to as "IPDI"), norbornane diisocyanate (hereinafter sometimes referred to as "NBDI"), hexamethylene diisocyanate (hereinafter referred to as "HDI"), hexylmethane diisocyanate (hereinafter referred to as "HMDI"), diphenylmethane diisocyanate (hereinafter referred to as "MDI"), and the like. In the present invention, these isocyanates may be used alone, or in a combination of two or more.

The proportions of the polyol, the isocyanate, and the flame-retarding agent in the flame-retardant urethane resin composition are appropriately determined in view of the target urethane resin product or the properties required for the urethane resin.

According to the intended purpose, the flame-retardant urethane resin composition of the present invention may further comprise an optional component or a combination of one or more optional components to the extent that the properties of the urethane resin are not impaired, so as to produce various types of urethane resins suitable for different purposes. Examples of the optional components include a chain extension agent, an antioxidant, various catalysts, a silane coupling agent, a filler, a thixotropy-imparting agent, a tackifier, wax, a thermal stabilizer, a light stabilizer, a fluorescent brightening agent, a thermoplastic resin, a thermosetting resin, a dye, a pigment, other flame-retarding agents, a conductivity-imparting agent, an antistatic agent, a moisture permeability improver, a water repellent, an oil repellent, a hollow foam, a crystallization water-containing compound, a water absorbent, a moisture absorbent, a deodorant, an antifungal agent, an antiseptic agent, an anti-algae agent, a pigment dispersant, an antiblocking agent, a hydrolysis inhibitor, and the like.

The flame-retardant urethane resin composition of the present invention can be preferably applied to synthetic leather. It is possible to provide synthetic leather having flame retardancy by forming a layer of the flame-retardant urethane resin composition of the present invention on at least one surface of the base fabric of synthetic leather.

Next, the flame-retardant synthetic leather of the present invention is described below. There is no particular limitation to the flame-retardant synthetic leather of the present invention, as long as it shows excellent flame retardancy due to a layer containing the flame-retardant urethane resin composition of the present invention formed on at least one surface of the base fabric. For example, the flame-retardant urethane resin composition of the present invention is used in a satisfactory manner as an adhesive layer of synthetic leather comprising a base fabric, an adhesive layer, and a surface skin layer in this order. In this manner, the flame-retardant urethane resin composition of the present invention can impart excellent flame retardancy to the synthetic leather itself. The flame-retardant synthetic leather of the present invention may comprise an intermediate layer arbitrarily formed between the adhesive layer and the surface skin layer.

The material of the base fabric of the flame-retardant synthetic leather of the present invention is suitably selected from among generally known materials. Examples include a woven fabric, a knitted fabric, and a nonwoven fabric, that are formed of a single fiber or a combination of fibers selected from among synthetic fibers, such as polyester, polyamide, and polyacrylonitrile; natural fibers, such as cotton and hemp; and regenerated fibers, such as rayon and acetate. There is no limitation to the material of the base fabric, but polyester fiber is preferable.

Examples of polyester fibers include, but are not particularly limited to, polyethylene terephthalate, polybutylene terephthalate, polytrimethylene terephthalate, and the like. These ethylene-based polymers may contain an acid component, such as adipic acid and isophthalic acid, or a diol, such as butanediol and diethylene glycol, without departing from the spirit of the present invention. In particular, polyethylene terephthalate, which has advantageous properties, such as versatility and strength, can be used in a satisfactory manner in the present invention. These polyester fibers in fabric may be used singly, or in a combination of two or more.

The base fabric is used in flame-retardant synthetic leather, and thus desirably has a property and a feature appropriate for its usage. For example, the base fabric of the present invention is preferably used in a flame-retardant synthetic leather for vehicles or furniture. When it is used for vehicles or furniture, in particular, a repetitive load is assumed to be applied. Against such a repetitive load, excellent restorability is required. It is also desirable to have excellent tearing strength or tensile strength.

There is no limitation to the surface skin layer used in the flame-retardant synthetic leather of the present invention, as long as the layer is formed of a synthetic resin and is known as a surface skin layer for synthetic leather. A surface skin layer of polyurethane-based resin, polyvinyl chloride-based resin, or acrylic-based resin is known. In particular, a surface skin layer of polyurethane-based resin, which has good processability or texture, is satisfactorily used.

As the surface skin layer of polyurethane-based resin, any known skin layers for synthetic leather formed of the following may be used: polycarbonate-based polyurethane, polyether-based polyurethane, polyester-based polyurethane, polyester/polyether-based polyurethane, lactone-based polyurethane, and the like. Of these, polycarbonate-based polyurethane, which has excellent durability or heat resistance, is suitably used to form a skin layer for synthetic leather for vehicles or furniture. In addition to these polyurethane resins, a high molecular weight polymer, such as natural rubber, chloroprene, SBR, acrylic-based resin, silicone-based resin, and vinyl chloride, may be used in combination. In the present invention, the thickness of the surface skin layer is not particularly limited, and is generally preferably about 20 to 200 μm.

The resin constituting the surface skin layer may optionally be mixed with various additives, such as a film-forming auxiliary agent, a coloring agent, a filler, a light stabilizer, a UV absorber, an antioxidant, and water or oil repellent.

There is no particular limitation to the adhesive layer of the flame-retardant synthetic leather of the present invention, as long as it can adhere the surface skin layer to the base fabric in a satisfactory manner and, when an intermediate layer is further present between the base fabric and the surface skin layer, adhere the intermediate layer to the base fabric in a satisfactory manner. In general, polyurethane-based resin is used as a resin constituting the adhesive layer of synthetic leather obtained through a dry process.

In the flame-retardant synthetic leather of the present invention, the polyurethane-based resin constituting the adhesive layer is preferably formed from the flame-retardant urethane resin composition of the present invention. To form the adhesive layer using the flame-retardant urethane resin composition of the present invention, it is possible to produce a polyurethane-based adhesive agent by mixing a polyol, an isocyanate, and a flame-retarding agent, which are the constituent components of the above-mentioned urethane resin composition of the present invention, in a solvent, such as methyl ethyl ketone (MEK), dimethylformamide (DMF), isopropyl alcohol, ethyl acetate, or toluene, optionally with a crosslinking agent and a crosslinking accelerator. When the adhesive layer is formed using the flame-retardant urethane resin composition of the present invention, and when flame retardancy is imparted to the synthetic leather only through this adhesive layer, it is sufficient if the adhesive layer comprises the flame-retarding agent in an amount of, for example, 1 to 50 wt %, preferably 3 to 40 wt %, and more preferably 5 to 30 wt %.

The flame-retardant synthetic leather of the present invention may be produced, for example, by a method similar to a hitherto known synthetic leather production method, such as a method comprising the following three steps.

First, in a first step, a resin composition for forming a surface skin layer is applied to a release paper, followed by drying to form a coating film serving as a surface skin layer.

As a second step, the following three methods are exemplified.

The first method comprises applying a flame-retardant urethane resin composition for constituting an adhesive layer to the upper surface of the coating film serving as a surface skin layer, and superimposing a base fabric and the surface skin layer so that the adhesive layer is sandwiched therebetween.

The second method comprises applying a flame-retardant urethane resin composition for constituting an adhesive layer to the surface of a base fabric, and superimposing the base fabric and the coating film serving as the surface skin layer so that the adhesive layer is sandwiched between the base fabric and the surface skin layer.

The third method comprises performing the first and second methods. Specifically, the third method comprises applying a flame-retardant urethane resin composition for constituting an adhesive layer to both the upper surface of the coating film serving as a surface skin layer and the surface of a base fabric, and superimposing the adhesive layers on each other.

Lastly, after the substrates are superimposed on each other by one of the three methods of the second step, a third step comprises bonding the substrates by a known compression method, such as ordinary temperature-compression bonding or thermo-compression bonding, and curing the resin constituting the adhesive layer.

The above method is a dry production method; however, the method for producing the flame-retardant synthetic leather of the present invention is not limited to this method. It is possible to use a known method, such as a wet production method, to produce the flame-retardant synthetic leather of the present invention. Regardless of the type of the production method, the synthetic leather comprises a base fabric, an adhesive layer, and a surface skin layer in this order. The synthetic leather may further comprise an intermediate layer arbitrarily formed between the adhesive layer and the surface skin layer. When a wet production method is used, it is possible to produce a synthetic leather having an intermediate layer, such as a microporous layer, between the base fabric and the adhesive layer.

The method for applying the resin composition may be any known method. The application may be performed by using, for example, a device, such as a roll coater, a gravure coater, a knife coater, a comma coater, and a T-die coater. There is no limitation to the release paper as long as it has mold releasability with respect to the resin constituting the surface skin layer. An olefin sheet or film of polyethylene resin or polypropylene resin is widely used, although it is not limited thereto. It is also possible to form the surface skin layer without using a release paper. For example, the surface skin layer may be formed by calendar processing. In the obtained synthetic leather, the thickness of the surface skin layer is not particularly limited, while the thickness of the adhesive layer is generally 20 to 200 μm, although it is not limited thereto.

The flame-retardant synthetic leather of the present invention comprises at least a layer formed of the flame-retardant urethane resin composition of the present invention, and thus shows flame retardancy in a satisfactory manner. This layer formed of the flame-retardant urethane resin composition is preferably an adhesive layer, but may also be a surface skin layer. When an intermediate layer is present, the intermediate layer may be formed of the flame-retardant urethane resin composition of the present invention.

To impart higher flame retardancy to the synthetic leather of the present invention, one or more flame-retarding agents other than the flame-retarding agent of the present invention may be used to impart flame retardancy to the base fabric, the adhesive layer, and/or the surface skin layer by a known means.

For example, when the base fabric is made of polyester fiber, methods for imparting flame retardancy to the base fabric are roughly categorized into the following methods: a method in which one or more flame-retarding agents other than that of the present invention are copolymerized, followed by spinning, in the production step of polyester; and a method in which polyester fiber is first produced and one or more flame-retarding agents other than that of the present invention are allowed to be exhausted into the polyester fiber. Either of these methods may be used. Examples of methods for imparting flame retardancy to the adhesive layer or surface skin layer include a method for adding one or more flame-retarding agents other than that of the present invention to the resin composition constituting the adhesive layer or the surface skin layer, and a method for copolymerizing the resin constituting the adhesive layer with one or more flame-retarding agents other than that of the present invention.

The above one or more flame-retarding agents other than that of the present invention are not particularly limited, and are preferably halogen-free flame-retarding agents in consideration of the spirit of the present invention.

EXAMPLES

The present invention is described in more detail with reference to Examples below. However, the scope of the present invention is not limited to these Examples.

Synthesis Example 1

Synthesis of a Compound of Formula (9)

[Chem. 11]

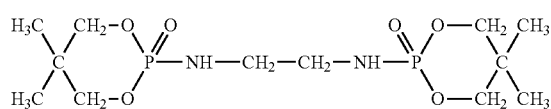

(9)

As the first step reaction, 312.6 g of neopentylglycol (3.00 mol) and 109.5 g of 1,4-dioxane were placed into a 1-L four-necked flask equipped with a stirrer, a thermometer, a reflux tube connected to a hydrochloric-acid-recovering device, an aspirator, a dropping funnel, and a heating device. The resulting mixture was heated to 50° C. Subsequently, 460.5 g of phosphorus oxychloride (3.00 mol) was added thereto over two hours while the reaction temperature was maintained at 45 to 55° C. After the completion of the addition, generated hydrochloric acid was collected while the mixture was stirred at 80° C. for 1 hour, followed by dehydrochlorination at 80° C. at a reduced pressure of 80 kPa for 3 hours to thereby obtain 662.8 g of a white slurry.

As the second step reaction, 443.4 g of the white slurry obtained above in the first step reaction and 370.2 g of 1,4-dioxane were placed into a 2-L four-necked flask equipped with a stirrer, a thermometer, a dropping funnel, and a water bath. While the reaction temperature was maintained at 30° C., 72.3 g of ethylenediamine (1.20 mol) was added over two hours. After the completion of the addition, the mixture was stirred at 30° C. for another 2 hours. Next, 364.2 g of a 24% aqueous sodium hydroxide solution (2.19 mol) was added thereto over 4.5 hours, while the reaction temperature was maintained at 20 to 30° C., and the obtained white slurry was filtrated. Then, a step of performing 30-minute repulp washing using water with the same weight as that of the filter cake and filtration was repeated until the filtrate was neutralized. The obtained solid was dried at 80° C. under 2.7 kPa for 8 hours to obtain 301.1 g of a flame-retardant compound comprising compound (9) as a main component (yield: 77.4%).

Phosphorus content: 17.1 wt %
Nitrogen content: 7.8 wt %

The obtained flame-retardant compound was ground to an average particle diameter of 20 μm or less, and used in the following Examples.

Synthesis Example 2

Synthesis of a Compound of Formula (14)

[Chem. 12]

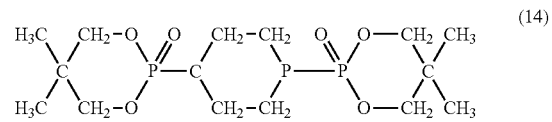

(14)

100.6 g of the white slurry obtained above in the first step reaction of Synthesis Example 1 and 214.3 g of 1,4-dioxane were placed into a 1-L four-necked flask equipped with a stirrer, a thermometer, a dropping funnel, and a water bath. While the reaction temperature was maintained at 30 to 40° C., 61.8 g of triethylamine (0.61 mol) was added thereto over 30 minutes. Subsequently, 23.4 g of piperazine (0.27 mol) was gradually added thereto over 2 hours. After the completion of the addition, the resulting mixture was stirred at 40° C. for 4 hours. Then, 169.3 g of water was added to this reaction slurry, and the mixture was stirred for 30 minutes, followed by filtration. Thereafter, a step of performing 30-minute repulp washing using water with the same weight as that of the filter cake and filtration was repeated until the filtrate was neutralized. The obtained solid was dried at 80° C. under 2.7 kPa for 8 hours to obtain 77.1 g of a flame-retardant compound comprising compound (14) as a main component (yield: 74%).

Phosphorus content: 15.6 wt %
Nitrogen content: 7.5 wt %

The obtained flame-retardant compound was ground to an average particle diameter of 20 μm or less, and used in the following Examples.

Example 1

0.7 part by weight of SN-thickener A-812 (produced by San Nopco Limited) was added as a thickener to 20 parts by weight of the flame-retardant compound obtained in Synthesis Example 1, 20 parts by weight of ion exchange water, 40 parts by weight of a commercially available acrylic resin emulsion (VONCOAT AB-886, produced by DIC Corporation; solids content: 50%), and 0.4 part by weight of a 28% aqueous ammonia solution. The resulting mixture was homogenized with a homogenizer to obtain a back-coating agent having a viscosity of 15,000 mPa·s (BM-type viscometer, No. 4 rotor, 12 rpm).

The back-coating agent obtained above was uniformly applied to the back surface of a polyester knit of 250 g/m² to a dry weight of 60 g/m², followed by drying at 150° C. for 3 minutes to thereby obtain a flame-retardant fiber fabric.

Example 2

A flame-retardant fiber fabric was obtained as in Example 1, except that the flame-retardant compound obtained in Synthesis Example 2 was used in an amount of 20 parts by weight as the flame-retardant compound.

Comparative Example 1

A flame-retardant fiber fabric was obtained as in Example 1, except that a silane-coated product of ammonium polyphosphate (FR CROS 486, produced by Budenheim; hereinafter referred to as "APP"), i.e., a polyphosphate-based flame-retarding agent, was used in an amount of 20 parts by weight as the flame-retardant compound.

Comparative Example 2

A flame-retardant fiber fabric was obtained as in Example 1, except that a compound having the following structure:

[Chem. 13]

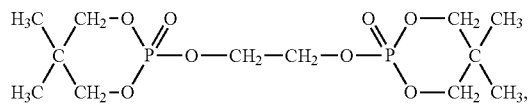

i.e., a phosphoric acid ester-based flame-retarding agent, was used in an amount of 20 parts by weight as the flame-retardant compound.

The flame retardancy of the flame-retardant fiber fabrics of Examples 1 and 2 and Comparative Examples 1 and 2, and the solubility in hot water of the flame-retardant compounds were measured.

Flame Retardancy Test

The flame retardancy test was performed in accordance with the test method of the U.S. Federal Motor Vehicle Safety Standards, FMVSS 302. The test was performed five times in both a horizontal and vertical direction; and when all of the test results satisfied any of the following, the tested fiber fabric was considered to have flame retardancy, and given a Pass designation: 1) self-extinguished before the marked line A (38 mm); 2) burnt length after the marked line A was 50 mm or less, and the burning time was 60 seconds or less; 3) the burning rate was 80 mm/min after the marked line A.

Solubility in Hot Water Test 5 g of the flame-retardant compound of Synthesis Example 1 or 2, or the flame-retardant compound of Comparative Example 1 or 2 was added to 45 g of water. The resulting mixture was stirred at 90° C. for 1 hour, and the phosphorus content in the filtrate obtained by filtration when the mixture was hot was measured to determine the solubility in hot water at 90° C. When the flame-retardant compound was fully dissolved, the solubility in hot water was regarded as ">10%."

Table 1 shows the results of the flame retardancy test and the solubility in hot water test, as well as the phosphorus content and nitrogen content of the flame-retardant compound used.

TABLE 1

|  | Phosphorus content of flame-retardant compound | Nitrogen content of flame-retardant compound | Flame retardancy | Solubility in hot water of flame-retardant compound |
|---|---|---|---|---|
| Example 1 | 17.1% | 7.8% | Pass | 0.7% |
| Example 2 | 15.6% | 7.6% | Pass | 0.4% |
| Comp. Ex. 1 | 31.3% | 14.1% | Pass | 5.9% |
| Comp. Ex. 2 | 17.3% | — | Failed | >10% |

As shown in Table 1, the fiber fabrics of Examples 1 and 2 have excellent flame retardancy, even though the phosphorus content and nitrogen content of the flame-retardant compounds of Examples 1 and 2 were less than those of the fiber fabric of Comparative Example 1. The phosphorus content and nitrogen content are believed to contribute to flame retardancy. Table 1 also shows that the flame-retardant compounds used in the fiber fabrics of Examples 1 and 2 have low solubility in hot water. The solubility in hot water is the cause of water spot formation. In contrast, the fiber fabric of Comparative Example 1, in which APP was used as the flame-retardant compound, was given a Pass designation in the flame retardancy test; however, this fiber fabric has high solubility in hot water, and thus easily suffers from the formation of water spots.

In Comparative Example 2, a phosphoric acid ester that shows excellent flame retardancy for use in a high-temperature exhaustion treatment for fiber was used as the flame-retardant compound. The flame-retardant compound of Comparative Example 2 is phosphoric acid ester having a structure similar to that of the flame-retardant compound of Example 1. The phosphorus content of the flame-retardant compound of Comparative Example 2 is also similar to that of the flame-retardant compound of Example 1. However, as shown in Table 1, the flame-retardant compound of Comparative Example 2 has insufficient flame retardancy and a high solubility in hot water, and is thus not suitable as a flame-retarding agent for back-coating. This demonstrates that a back-coating agent comprising the phosphoramidate represented by Formula (I) is very effective as a flame-retardant back-coating agent.

Example 3

Production of Surface Skin Layer

Toluene was mixed in an amount of 30 parts by weight per 100 parts by weight of a polyurethane material (produced by DIC Corporation, CRISVON MP120; nonvolatile component: 30 wt %) to prepare a solution as a resin composition for forming a surface skin layer.

Thereafter, the resin composition solution for forming the surface skin layer prepared above was applied to a release paper (produced by Dai Nippon Printing Co., Ltd., DE73) using an applicator set to 320 μm. The resulting coating film was dried at 110° C. for 4 minutes to form a coating film serving as a surface skin layer having an average dry film thickness of 40 μm.

Preparation of Resin Composition for Forming Adhesive Layer

A resin composition for forming an adhesive layer was prepared by using 100 parts by weight of a polyurethane material for adhesion (produced by DIC Corporation, CRISVON 4010; nonvolatile component: 50 wt %), 10 parts by weight of an isocyanate-based crosslinking agent (produced by DIC Corporation, BURNOCK D-750; nonvolatile component: 75 wt %), 3 parts by weight of a crosslinking accelerator (produced by DIC Corporation, CRISVON Accel HM, nonvolatile component: 15 wt %), 6.45 parts by weight of the flame-retardant compound of Synthesis Example 1 (nonvolatile component: 100 wt %) as a flame-retarding agent, and 22.8 parts by weight of toluene.

Preparation of Synthetic Leather

The resin composition for forming an adhesive layer prepared above was applied to the upper surface of the coating film serving as a surface skin layer obtained above by using an applicator set to 320 μm, and a base fabric (a polyester knit; weight per area: 250 g/m$^2$) was laminated thereon, followed by pressure bonding. The resulting product was heated at 110° C. for 4 minutes to accelerate curing while the solvent was being removed. Then, aging was performed at 25° C. for three days to complete the curing of the adhesive layer, and the release paper was peeled off to complete a flame-retardant synthetic leather. The adhesive layer had a thickness of 150 μm.

Flame Retardancy Test

The flame retardancy test was performed on the above flame-retardant synthetic leather in accordance with the test method of the Federal Motor Vehicle Safety Standards, FMVSS 302.

The test was performed a total of 5 times, and when self-extinguishment was observed before the marked line A (38 mm) in all of the test results, the leather was determined as having flame retardancy and given a Pass designation. Table 2 shows the results.

Example 4

A synthetic leather was obtained as in Example 3, except that the flame-retardant compound of Synthesis Example 2 was used as the flame-retarding agent, and the flame retardancy was measured. Table 2 shows the results.

Comparative Example 3

A synthetic leather was obtained as in Example 3, except that the phosphoric acid ester flame-retardant compound used in Comparative Example 2 was used as the flame-retarding agent, and the flame retardancy was measured. Table 2 shows the results.

Comparative Example 4

A synthetic leather was obtained as in Example 3, except that 20 parts by weight of tetrakis(2,6-dimethylphenyl)-m-phenylenebisphosphate, which is a phosphoric acid ester that is widely used for resin as the flame-retarding agent, and 39.2 parts by weight of toluene were used; and the flame retardancy was measured. Table 2 shows the results.

TABLE 2

| | Phosphorus content of flame-retardant compound (wt %) | Flame-retardant compound content of adhesive layer (wt %) | Maximum burnt length in flame retardant test (mm) | Flame retardancy |
|---|---|---|---|---|
| Example 3 | 17.1 | 10 | 13 | Pass |
| Example 4 | 15.6 | 10 | 27 | Pass |
| Comp. Ex. 3 | 17.3 | 10 | 44 | Failed |
| Comp. Ex. 4 | 9.0 | 25.7 | 48 | Failed |

As shown in Table 2, the synthetic leathers of Examples 3 and 4 show higher flame retardancy than the synthetic leathers of Comparative Examples 3 and 4, which used a phosphoric acid ester having excellent flame retardancy for use in a high-temperature exhaustion treatment for fiber.

INDUSTRIAL APPLICABILITY

The flame-retarding agent of the present invention has excellent flame retardancy and is environmentally friendly because it is halogen-free. Further, the flame-retarding agent of the present invention does not cause the formation of water spots, since it has low solubility in hot water. The use of the flame-retardant aqueous resin composition comprising the flame-retarding agent of the present invention as a back-coating agent to back-coat a fiber fabric can produce a flame-retardant fiber fabric that has excellent flame retardancy, and that is free from water spots.

Additionally, the use of the flame-retardant urethane resin composition comprising the flame-retarding agent of the present invention can produce a flame-retardant synthetic leather with excellent flame retardancy.

The thus-obtained flame-retardant fabric and flame-retardant synthetic leather can be used for various purposes.

We claim:

1. A flame-retarding agent comprising a phosphoramidate compound represented by Formula (I):

[Chem. 1]

$$\begin{array}{c} R_1 \\ \diagdown \\ R_2 \end{array} C \begin{array}{c} R_{11}-O \\ \diagdown \\ R_{11}-O \end{array} \begin{array}{c} O \\ \diagup\!\!\!\diagdown \\ P \end{array} \begin{array}{c} R_{13}-A \\ \diagup \\ N \\ \diagdown \\ B_1 \end{array} \quad (I)$$

wherein $R_1$ and $R_2$ are each independently $C_{1-3}$ alkyl, $R_{11}$ and $R_{12}$ are each independently $C_{1-3}$ alkylene, $R_{13}$ is $C_{1-6}$ alkylene, $B_1$ is hydrogen, and A is an organic group represented by Formula (Ia):

[Chem. 2]

$$\begin{array}{c} \diagdown \\ N-P \\ \diagup \\ B_2 \end{array} \begin{array}{c} O \\ \diagup\!\!\!\diagdown \\ O-R_{15} \end{array} \begin{array}{c} O-R_{14} \\ \diagup \\ C \\ \diagdown \\ R_4 \end{array} \quad (Ia)$$

wherein $R_3$ and $R_4$ are each independently methyl, $R_{14}$ and $R_{15}$ are each independently methylene, and $B_2$ is hydrogen.

2. The flame-retarding agent according to claim 1, wherein in Formula (I), $R_1$ and $R_2$ represent methyl, and $R_{11}$ and $R_{12}$ represent methylene.

3. The flame-retarding agent according to claim 1, wherein $R_{13}$ of Formula (I) is $C_{1-4}$ alkylene.

4. The flame-retarding agent according to claim 3, wherein $R_{13}$ of Formula (I) is $C_{1-2}$ alkylene.

5. A flame-retardant aqueous resin composition comprising: a flame-retarding agent comprising a phosphoramidate compound represented by Formula (I):

[Chem. 3]

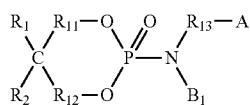
(I)

wherein $R_1$ and $R_2$ are each independently $C_{1-3}$ alkyl, $R_{11}$ and $R_{12}$ are each independently $C_{1-3}$ alkylene, $R_{13}$ is $C_{1-6}$ alkylene, $B_1$ is hydrogen or $C_{1-6}$ alkyl, and A is hydrogen or an organic group represented by Formula (Ia):

[Chem. 4]

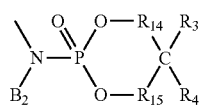
(Ia)

wherein $R_3$ and $R_4$ are each independently $C_{1-3}$ alkyl, $R_{14}$ and $R_{15}$ are each independently $C_{1-3}$ alkylene, and $B_2$ is hydrogen or $C_{1-6}$ alkyl,
wherein when $B_1$ is $C_{1-6}$ alkyl, and A is hydrogen, $B_1$ and $R_{13}$-A, taken together with nitrogen to which they are attached, may form a non-aromatic nitrogen-containing heterocycle, and wherein when $B_1$ is $C_{1-6}$ alkyl, A is an organic group represented by Formula (Ia), and $B_2$ is $C_{1-6}$ alkyl, $B_1$ and $B_2$, taken together with nitrogen to which they are attached and with $R_{13}$, may form a non-aromatic nitrogen-containing heterocycle; and
an aqueous resin emulsion.

6. A back-coating agent comprising the flame-retardant aqueous resin composition of claim 5.

7. A flame-retardant fiber fabric back-coated with the back-coating agent of claim 6.

8. A coating agent comprising the flame-retardant aqueous resin composition of claim 5.

9. A flame-retardant urethane resin composition for synthetic leather, the composition comprising: a flame-retarding agent comprising a phosphoramidate compound represented by Formula (1):

[Chem. 5]

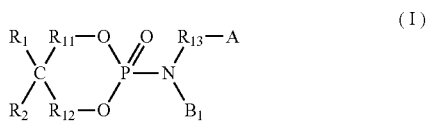
(I)

wherein $R_1$ and $R_2$ are each independently $C_{1-3}$ alkyl, $R_{11}$ and $R_{12}$ are each independently $C_{1-3}$ alkylene, $R_{13}$ is $C_{1-6}$ alkylene, $B_1$ is hydrogen or $C_{1-6}$ alkyl, and A is hydrogen or an organic group represented by Formula (Ia):

[Chem. 6]

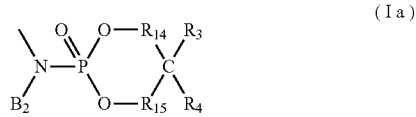
(Ia)

wherein $R_3$ and $R_4$ are each independently $C_{1-3}$ alkyl, $R_{14}$ and $R_{15}$ are each independently $C_{1-3}$ alkylene, and $B_2$ is hydrogen or $C_{1-6}$ alkyl,
wherein when $B_1$ is $C_{1-6}$ alkyl, and A is hydrogen, $B_1$ and $R_{13}$-A, taken together with nitrogen to which they are attached, may form a non-aromatic nitrogen-containing heterocycle, and
wherein when $B_1$ is $C_{1-6}$ alkyl, A is an organic group represented by Formula (Ia), and $B_2$ is $C_{1-6}$ alkyl, $B_1$ and $B_2$, taken together with nitrogen to which they are attached and with $R_{13}$, may form a non-aromatic nitrogen-containing heterocycle;
a polyol; and
an isocyanate.

10. A flame-retardant synthetic leather having on at least one surface of a base fabric a layer containing the flame-retardant urethane resin composition of claim 9.

11. The flame-retardant synthetic leather according to claim 10, wherein the flame-retardant synthetic leather comprises at least a base fabric, an adhesive layer, and a surface skin layer in this order, and the adhesive layer is formed of the flame-retardant urethane resin composition of claim 9.

* * * * *

UNITED STATES PATENT AND TRADEMARK OFFICE
CERTIFICATE OF CORRECTION

| | |
|---|---|
| PATENT NO. | : 10,000,625 B2 |
| APPLICATION NO. | : 14/411906 |
| DATED | : June 19, 2018 |
| INVENTOR(S) | : Takehiro Ueki, Tomoe Takemoto and Hiroshi Tsuji |

It is certified that error appears in the above-identified patent and that said Letters Patent is hereby corrected as shown below:

In the Claims

In Claim 1, after Line 3 in Formula (I) (Column 20, Line (49)), the instance of "$R_{11}$" at the bottom of Formula (I) should read --$R_{12}$--.

Signed and Sealed this
Fourth Day of June, 2024

Katherine Kelly Vidal
*Director of the United States Patent and Trademark Office*